United States Patent
Watanabe et al.

(10) Patent No.: US 10,434,091 B2
(45) Date of Patent: Oct. 8, 2019

(54) AGENT FOR TREATING AND/OR PREVENTING ADULT T CELL LEUKEMIA/LYMPHOMA

(71) Applicants: DAIICHI SANKYO COMPANY, LIMITED, Tokyo (JP); THE UNIVERSITY OF TOKYO, Tokyo (JP)

(72) Inventors: Toshiki Watanabe, Tokyo (JP); Makoto Yamagishi, Tokyo (JP); Osamu Kanno, Tokyo (JP); Jun Watanabe, Tokyo (JP); Nobuaki Adachi, Tokyo (JP); Daisuke Honma, Tokyo (JP); Yoshito Hamada, Tokyo (JP)

(73) Assignees: DAIICHI SANKYO COMPANY, LIMITED, Tokyo (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/742,478

(22) PCT Filed: Jul. 29, 2016

(86) PCT No.: PCT/JP2016/072262
§ 371 (c)(1),
(2) Date: Jan. 5, 2018

(87) PCT Pub. No.: WO2017/018499
PCT Pub. Date: Feb. 2, 2017

(65) Prior Publication Data
US 2018/0200238 A1    Jul. 19, 2018

(30) Foreign Application Priority Data
Jul. 30, 2015  (JP) .................. 2015-151170

(51) Int. Cl.
A61K 31/443    (2006.01)
A61P 35/02     (2006.01)
C07D 405/12    (2006.01)

(52) U.S. Cl.
CPC ............ *A61K 31/443* (2013.01); *A61P 35/02* (2018.01); *C07D 405/12* (2013.01)

(58) Field of Classification Search
None
See application file for complete search history.

(56) References Cited

U.S. PATENT DOCUMENTS

| | | |
|---|---|---|
| 2006/0183794 A1 | 8/2006 | Umezawa et al. |
| 2009/0012031 A1 | 1/2009 | Chinnaiyan et al. |
| 2011/0263566 A1 | 10/2011 | Matsuo et al. |
| 2017/0073335 A1* | 3/2017 | Kanno |

FOREIGN PATENT DOCUMENTS

| | | |
|---|---|---|
| JP | 2012-507525 A | 3/2012 |
| JP | WO 2015/141616 A1 * | 9/2015 |
| WO | WO-2004/002465 A1 | 1/2004 |

OTHER PUBLICATIONS

Yoshimitsu et al., "Prevention of human T-cell lymphotropic virus type 1 infection and adult T-cell leukemia/lymphoma", Recent Results in Cancer Research, 2014, vol. 193, pp. 211-225; Abstract only (Year: 2014).*
Yamaguchi K et al. (2002), "Human T Lymphotropic Virus Type-I and Adult T-Cell Leukemia in Japan", Int J Hematol 2002; 76 Suppl 2: 240-245.
Iwanaga M et al. (2010), "Human T-cell leukemia virus type I (HTLV-1) proviral load and disease progression in asymptomatic HTLV-1 carriers: a nationwide prospective study in Japan", Blood 2010, 116(8): 1211-1219.
Vose J M et al. (2008), "International Peripheral T-Cell and Natural Killer/T-Cell Lymphoma Study: Pathology Findings and Clinical Outcomes", J Clin Oncol 2008, 26(25): 4124-30.
Tsukasaki K et al. (2007), "VCAP-AMP-VECP Compared With Biweekly CHOP for Adult T-Cell Leukemia-Lymphoma: Japan Clinical Oncology Group Study JCOG9801", J Clin Oncol 2007, 25(34): 5458-64.
Ishida T et al. (2012), "Defucosylated Anti-CCR4 Monoclonal Antibody (KW-0761) for Relapsed Adult T-Cell Leukemia-Lymphoma: A Multicenter Phase II Study", J Clin Oncol 2012, 30(8): 837-42.
Yamagishi M et al. (2012), "Polycomb-Mediated Loss of miR-31 Activates NIK-Dependent NF-kB Pathway in Adult T Cell Leukemia and Other Cancers", Cancer Cell 2012, 21: 121-135.
Yamagishi M et al. (2012), "Molecular hallmarks of adult T cell leukemia", Front Microbiol 2012, 3: 334, pp. 1-16.
Shen X et al. (2008), "EZH1 Mediates Methylation on Histone H3 Lysine 27 and Complements EZH2 in Maintaining Stem Cell Identity and Executing Pluripotency", Mol Cell 2008, 32(4): 491-502.

(Continued)

*Primary Examiner* — Savitha M Rao
*Assistant Examiner* — Gregg Polansky
(74) *Attorney, Agent, or Firm* — Foley & Lardner LLP

(57) ABSTRACT

The present invention provides an agent for treating and/or preventing adult T cell leukemia/lymphoma containing a compound having a specific chemical structure or a pharmaceutically acceptable salt thereof. Specifically, the present invention provides an agent for treating and/or preventing adult T cell leukemia/lymphoma containing, as an active ingredient, 7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, or 7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

8 Claims, 4 Drawing Sheets
Specification includes a Sequence Listing.

(56) References Cited

OTHER PUBLICATIONS

Sparmann A et al. (2006), "Polycomb silencers control cell fate, development and cancer", Nat Rev Cancer 2006, 6: 846-856.
Lund K et al. (2014), "EZH2 in normal and malignant hematopoiesis", Leukemia 2014, 28(1): 44-49.
Sasaki D et al. (2011), "Overexpression of enhancer of zeste homolog 2 with trimethylation of lysine 27 on histone H3 in adult T-cell leukemia/lymphoma as a target for epigenetic therapy", Haematologica 2011, 96(5): 712-719.
McCabe M T et al. (2012), "EZH2 inhibition as a therapeutic strategy for lymphoma with EZH2-activating mutations", Nature 2012, vol. 492, pp. 108-112.
International Search Report for International Application No. PCT/JP2016/072262 dated Sep. 13, 2016.
Bazarbachi et al, How I treat adult T-cell leukemia/lymphoma, Blood, 2011, vol. 118, No. 7, pp. 1736-1745.
Extended European Search Report dated Feb. 13, 2019 in corresponding application No. 16830602.5.

\* cited by examiner

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: forward primer pX2-S

<400> SEQUENCE: 1
cggataccca gtctacgtgt t                                          21

<210> SEQ ID NO 2
<211> LENGTH: 20
<212> TYPE: DNA
<213> ORGANISM: Artificial Sequence
<220> FEATURE:
<223> OTHER INFORMATION: reverse primer pX2-AS

<400> SEQUENCE: 2
cagtagggcg tgacgatgta                                            20

<210> SEQ ID NO 3
<211> LENGTH: 23
<212> TYPE: DNA
<213> ORGANISM: Artificial Sequence
<220> FEATURE:
<223> OTHER INFORMATION: FAM-labeled pX2 probe

<400> SEQUENCE: 3
ctgtgtacaa ggcgactggt gcc                                        23
```

AGENT FOR TREATING AND/OR PREVENTING ADULT T CELL LEUKEMIA/LYMPHOMA

CROSS REFERENCE TO RELATED APPLICATIONS

The present application is a U.S. national stage application of International Patent Application No. PCT/JP2016/072262, filed on Jul. 29, 2016, which claims the benefit of priority to Japanese Patent Application No. 2015-151170, filed on Jul. 30, 2015, the entireties of which are incorporated herein by reference.

TECHNICAL FIELD

The present invention relates to an agent for treating and/or preventing adult T cell leukemia/lymphoma containing a compound having a specific chemical structure or a pharmaceutically acceptable salt thereof.

BACKGROUND ART

In adult T cell leukemia/lymphoma (ATL), a plurality of genetic abnormalities are accumulated in HTLV-1 infected peripheral blood T cells during a long latent period of 50 to 60 years, which can cause malignant transformation. It is presumed that there are 20 million or more human adult T-cell leukemia virus type I (HTLV-1) infected persons (carriers) in the world, and it is presumed that there are 1.08 million or more infected persons, and ATL develops in about 1200 persons every year in Japan (Non Patent Literature 1). It has been revealed, as a result of cohort study, that ATL develops only in carriers in which a ratio of HTLV-1 infected cells in peripheral blood (provirus load, PVL) is 4% or more (Non Patent Literature 2). This group of persons with high risk of development occupies 25% in the entire carriers, and it is expected that reduction of the number of infected cells would lead to reduction of risk of the ATL development. There are, however, a large number of unclear points in molecular mechanisms of immortalization and tumorigenesis of cells caused by HTLV-1 and of refractoriness, and there has been found neither an effective method for treating ATL nor a method for selectively removing infected cells. Owing to appearance of an anti-CCR4 antibody, that is, a molecular target drug against ATL, the treatment outcome has been improved, but the prognosis is still the worst among those of malignant lymphomas (Non Patent Literature 3), and in terms of median survival, the treatment outcome of chemotherapy for acute ATL is 12.7 months (Non Patent Literature 4) and the treatment outcome by the CCR4 antibody against recurrence is 13.7 months (Non Patent Literature 5). Accordingly, it is imperative, based on medical condition elucidation at the molecular level, to prevent the virus infection, to prevent the leukemia development and to develop a novel treatment method.

It has been revealed, as a result of large scale analysis of gene expression using a large number of ATL clinical samples, that ATL cells are a population having a very uniform and abnormal gene expression pattern (Non Patent Literature 6). Besides, ATL cells have characteristic signal transduction system abnormality, which corresponds to a key of survival and growth of tumor cells, and it has been revealed that the abnormality is derived from accumulation of epigenetic abnormalities (Non Patent Literature 7).

The polycomb family negatively controls gene expression through chromatin control by histone modification. Enhancer of Zeste Homologue 1/2 (EZH1/2) corresponds to active center of Polycomb Repressive Complex 2 (PRC2) that trimethylates histone H3K27. EZH1 and EZH2 retain an epigenome in a cell while mutually compensating their functions. Inhibition of EZH2 leads to reduction of methylation level of H3K27 throughout the cell, but this effect is restricted by the compensating effect of EZH1. When EZH1 and EZH2 are simultaneously inhibited, the methylation can be more effectively eliminated (Non Patent Literature 8). It has been found that abnormality in a PRC2 component leads to cancer or abnormality in stem cell function, and in particular, accumulation of methylated H3K27me3 induced by gene abnormality or increased expression of EZH2 is identified in a large number of cancers, and earnest studies are being conducted mainly for EZH2 as a novel cancer molecular target drug (Non Patent Literatures 9 and 10).

The abnormality of polycomb family occurring in ATL was cleared by exhaustive gene expression analysis (Non Patent Literatures 6 and 11). In particular, overexpression of EZH2 is conspicuous, and increase of the methylation level of H3K27 in the entire cells is also detected. Besides, it has been cleared that EZH2-dependent inhibition of miR-31 results in expression of NF-κB Inducing Kinase (NIK) so as to constitutively activate NF-κB pathway, and hence, EZH2 is regarded as effective as a molecular target drug against ATL.

CITATION LIST

Non Patent Literature

Non Patent Literature 1: Yamaguchi K., Watanabe T., Int J Hematol 2002; 76 Suppl 2: 240
Non Patent Literature 2: Iwanaga, M. et al., Blood 2010; 116 (8): 1211-9
Non Patent Literature 3: Vose, Armitage, J. et al., J Clin Oncol 2008; 26(25): 4124-30
Non Patent Literature 4: Utsunomiya A. et al., J Clin Oncol 2007; 25(34): 5458-64
Non Patent Literature 5: Ishida, Joh, et al., J Clin Oncol 2012; 30(8): 837-42
Non Patent Literature 6: Yamagishi M. et al., Cancer Cell 2012; 21: 121
Non Patent Literature 7: Yamagishi M., Watanabe T., Front Microbiol 2012; 3: 334
Non Patent Literature 8: Shen, X. et al., Mol Cell 2008; 32(4): 491-502
Non Patent Literature 9: Sparmann A., van Lohuizen M., Nat Rev Cancer 2006; 6: 846
Non Patent Literature 10: Lund, Adams, Copland., Leukemia 2014; 28(1): 44-9
Non Patent Literature 11: Sasaki D. et al., Haematologica 2011; 96: 712

SUMMARY OF INVENTION

Technical Problem

The present invention provides an agent for treating and/or preventing adult T cell leukemia/lymphoma containing a compound having a specific chemical structure or a pharmaceutically acceptable salt thereof.

Solution to Problem

The present inventors have cleared that (2R)-7-chloro-2-[trans-4-(dimethylamino)cyclohexyl]-N-[(4,6-dimethyl-2- oxo-1,2-dihydropyridin-3-yl)methyl]-2,4-dimethyl-1,3-benzodioxole-5-carboxamide or a pharmaceutically acceptable salt thereof, or (2R)-7-bromo-2-[trans-4-(dimethylamino) cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof is remarkably effective for treating and preventing adult T cell leukemia/lymphoma. The present invention was accomplished on the basis of this finding.

According to the present invention, inventions according to the following [1] to [34] are provided.

[1] An agent for treating and/or preventing adult T cell leukemia/lymphoma, comprising, as an active ingredient, 7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, or 7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[2] An agent for treating and/or preventing adult T cell leukemia/lymphoma, comprising, as an active ingredient, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, or (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[3] An agent for treating adult T cell leukemia/lymphoma, comprising, as an active ingredient, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[4] An agent for preventing adult T cell leukemia/lymphoma, comprising, as an active ingredient, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[5] An agent for treating adult T cell leukemia/lymphoma, comprising, as an active ingredient, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluenesulfonate.

[6] An agent for preventing adult T cell leukemia/lymphoma, comprising, as an active ingredient, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluenesulfonate.

[7] An agent for treating adult T cell leukemia/lymphoma, comprising, as an active ingredient, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[8] An agent for preventing adult T cell leukemia/lymphoma, comprising, as an active ingredient, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[9] A method for treating adult T cell leukemia/lymphoma in a patient suffering from adult T cell leukemia/lymphoma, comprising administering, to the patient, 7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, or 7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[10] A method for treating adult T cell leukemia/lymphoma in a patient suffering from adult T cell leukemia/lymphoma, comprising administering, to the patient, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[11] A method for treating adult T cell leukemia/lymphoma in a patient suffering from adult T cell leukemia/lymphoma, comprising administering, to the patient, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[12] A method for preventing onset of adult T cell leukemia/lymphoma in a subject of a human adult T cell leukemia virus type I (HTLV-1) carrier, comprising administering, to the subject, 7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, or 7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[13] A method for preventing onset of adult T cell leukemia/lymphoma in a subject of a human adult T cell leukemia virus type I (HTLV-1) carrier, comprising administering, to the subject, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[14] A method for preventing onset of adult T cell leukemia/lymphoma in a subject of a human adult T cell leukemia virus type I (HTLV-1) carrier, comprising administering, to the subject, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[15] Use of 7-chloro-2-[trans-4-(dimethylamino)cyclohexyl]-N-[(4,6-dimethyl-2-oxo-1,2-dihydropyridin-3-yl) methyl]-2,4-dimethyl-1,3-benzodioxole-5-carboxamide or a pharmaceutically acceptable salt thereof, or 7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, in the manufacture of a pharmaceutical composition for use in treating adult T cell leukemia/lymphoma in a patient suffering from adult T cell leukemia/lymphoma.

[16] Use of (2R)-7-chloro-2-[trans-4-(dimethylamino)cyclohexyl]-N-[(4,6-dimethyl-2-oxo-1,2-dihydropyridin-3-yl) methyl]-2,4-dimethyl-1,3-benzodioxole-5-carboxamide or a pharmaceutically acceptable salt thereof, in the manufacture of a pharmaceutical composition for use in treating adult T cell leukemia/lymphoma in a patient suffering from adult T cell leukemia/lymphoma.

[17] Use of (2R)-7-chloro-2-[trans-4-(dimethylamino)cyclohexyl]-N-[(4,6-dimethyl-2-oxo-1,2-dihydropyridin-3-yl) methyl]-2,4-dimethyl-1,3-benzodioxole-5-carboxamide

[18] Use of (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, in the manufacture of a pharmaceutical composition for use in treating adult T cell leukemia/lymphoma in a patient suffering from adult T cell leukemia/lymphoma.

[19] Use of 7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, or 7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, in the manufacture of a pharmaceutical composition for use in preventing onset of adult T cell leukemia/lymphoma in a subject of a human adult T cell leukemia virus type I (HTLV-1) carrier.

[20] Use of (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, in the manufacture of a pharmaceutical composition for use in preventing onset of adult T cell leukemia/lymphoma in a subject of a human adult T cell leukemia virus type I (HTLV-1) carrier.

[21] Use of (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluenesulfonate, in the manufacture of a pharmaceutical composition for use in preventing onset of adult T cell leukemia/lymphoma in a subject of a human adult T cell leukemia virus type I (HTLV-1) carrier.

[22] Use of (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, in the manufacture of a pharmaceutical composition for use in preventing onset of adult T cell leukemia/lymphoma in a subject of a human adult T cell leukemia virus type I (HTLV-1) carrier.

[23]: A pharmaceutical composition for use in reducing growth of adult T cell leukemia/lymphoma, lowering a survival rate of adult T cell leukemia/lymphoma, and/or killing adult T cell leukemia/lymphoma, comprising 7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, or 7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[24]: A pharmaceutical composition for use in reducing growth of adult T cell leukemia/lymphoma, lowering a survival rate of adult T cell leukemia/lymphoma, and/or killing adult T cell leukemia/lymphoma, comprising (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[25]: A pharmaceutical composition for use in reducing growth of adult T cell leukemia/lymphoma, lowering a survival rate of adult T cell leukemia/lymphoma, and/or killing adult T cell leukemia/lymphoma, comprising (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluenesulfonate.

[26]: A pharmaceutical composition for use in reducing growth of adult T cell leukemia/lymphoma, lowering a survival rate of adult T cell leukemia/lymphoma, and/or killing adult T cell leukemia/lymphoma, comprising (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[27]: A method for reducing growth of adult T cell leukemia/lymphoma, lowering a survival rate of adult T cell leukemia/lymphoma, and/or killing adult T cell leukemia/lymphoma in a subject in need thereof, comprising administering, to the subject, 7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, or 7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[28]: A method for reducing growth of adult T cell leukemia/lymphoma, lowering a survival rate of adult T cell leukemia/lymphoma, and/or killing adult T cell leukemia/lymphoma in a subject in need thereof, comprising administering, to the subject, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[29]: A method for reducing growth of adult T cell leukemia/lymphoma, lowering a survival rate of adult T cell leukemia/lymphoma, and/or killing adult T cell leukemia/lymphoma in a subject in need thereof, comprising administering, to the subject, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluenesulfonate.

[30]: A method for reducing growth of adult T cell leukemia/lymphoma, lowering a survival rate of adult T cell leukemia/lymphoma, and/or killing adult T cell leukemia/lymphoma in a subject in need thereof, comprising administering, to the subject, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

[31]: Use of 7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, or 7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, in the manufacture of a pharmaceutical composition for use in reducing growth of adult T cell leukemia/lymphoma, lowering a survival rate of adult T cell leukemia/lymphoma, and/or killing adult T cell leukemia/lymphoma.

[32]: Use of (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, in the manufacture of a pharmaceutical composition for use in reducing growth of adult T cell leukemia/lymphoma, lowering a survival rate of adult T cell leukemia/lymphoma, and/or killing adult T cell leukemia/lymphoma.

[33]: Use of (2R)-7-chloro-2-[trans-4-(dimethylamino) cyclohexyl]-N-[(4,6-dimethyl-2-oxo-1,2-dihydropyridin-3-yl)methyl]-2,4-dimethyl-1,3-benzodioxole-5-carboxamide p-toluenesulfonate, in the manufacture of a pharmaceutical composition for use in reducing growth of adult T cell leukemia/lymphoma, lowering a survival rate of adult T cell leukemia/lymphoma, and/or killing adult T cell leukemia/lymphoma.

[34]: Use of (2R)-7-bromo-2-[trans-4-(dimethylamino) cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, in the manufacture of a pharmaceutical composition for use in reducing growth of adult T cell leukemia/lymphoma, lowering a survival rate of adult T cell leukemia/lymphoma, and/or killing adult T cell leukemia/lymphoma.

The compound of the present invention or the pharmaceutically acceptable salt thereof is useful for preventing and/or treating ATL.

BRIEF DESCRIPTION OF DRAWINGS

FIG. 1 FIGS. 1A and 1B illustrate growth of cell line TL-Om1 derived from ATL patient tumor cells having been treated with a compound of Example 1 over time (FIG. 1A) and dose-dependently (FIG. 1B). The growth is plotted such that cell growth of a DMSO-treated group is 100%.

FIG. 2 FIGS. 2A and 2B illustrate growth of cell line TL-Om1 derived from ATL patient tumor cells having been treated with a compound of Example 3 over time (FIG. 2A) and dose-dependently (FIG. 2B). The growth is plotted such that cell growth of a DMSO-treated group is 100%.

DESCRIPTION OF EMBODIMENT

Figure 1A:
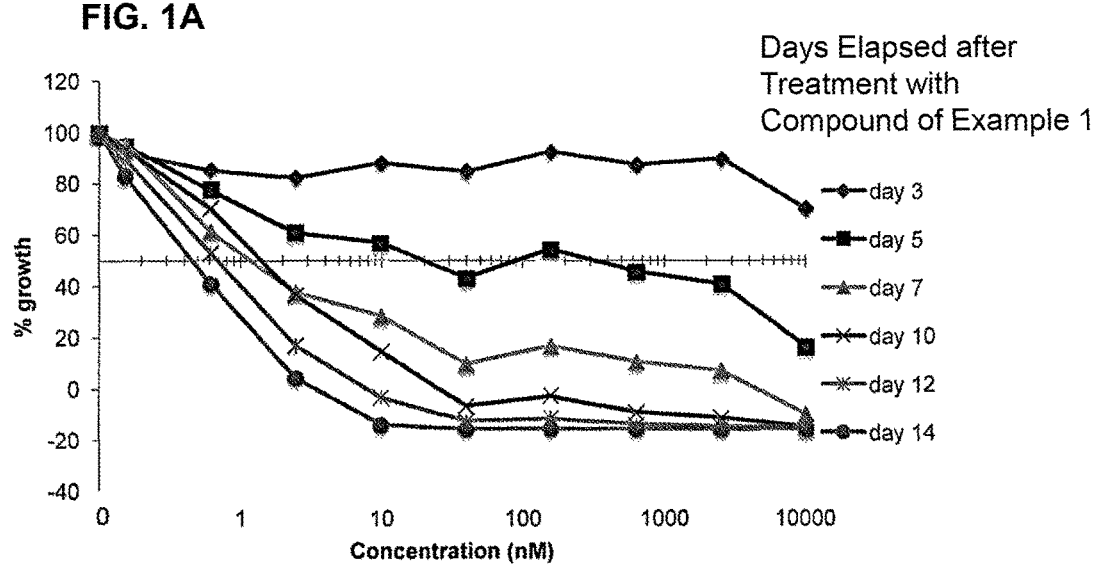

Herein, the term "adult T cell leukemia/lymphoma" (hereinafter, sometimes simply referred to "ATL") refers to leukemia/lymphoma caused by infection with human T cell leukemia virus type 1 (HTLV-1). ATL is sometimes designated also as "adult T cell leukemia" or "adult T cell lymphoma".

Herein, the term "HTLV-1 carrier" means a subject (a warm-blooded animal, particularly a human) infected with HTLV-1 virus. If a subject has an antibody to HTLV-1, the subject can be regarded as an HTLV-1 carrier.

Herein, the term "prevent" and derivatives thereof mean that the onset rate of ATL in an HTLV-1 carrier before the onset of ATL is reduced. The term means that the onset of ATL is prevented in preferably 60% or more, and more preferably 80% or more of subjects belonging to an HTLV-1 carrier group.

Herein, the term "treat" and derivatives thereof mean remission, relief, and/or delay of worsening of ATL clinical symptoms in a patient that has developed ATL.

A physician can diagnose ATL based on clinical symptoms of a subject. Besides, ATL is a disease caused by monoclonal growth of T cells in which HTLV-1 has been incorporated into the genome as a provirus, and hence ATL can be diagnosed by detecting, by a Southern blot method or the like, that HTLV-1 provirus is monoclonally incorporated into a DNA of ATL cells contained in a sample obtained from a subject.

As a test method for diagnosing that a subject is an HTLV-1 carrier, a particle agglutination assay (PA assay), a chemiluminescence assay, an indirect fluorescent antibody assay using a virus-infected cell as an antigen, and a Western blot method are known, and any of these can be appropriately employed. In the Western blot method, if an antibody to virus envelope protein (gp46) is positive and one or more antibodies to three core proteins (p19, p24 and p53) are positive in a sample obtained from a subject, it can be diagnosed that the subject is an HTLV-1 carrier. Alternatively, it can be subsidiarily diagnosed, by a polymerase chain reaction (PCR) for amplifying HTLV-1 provirus genome, whether or not the subject is a carrier.

According to the present invention, any of the following compounds and pharmaceutically acceptable salts thereof can be used for preventing and/or treating ATL.

(2R)-7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof:

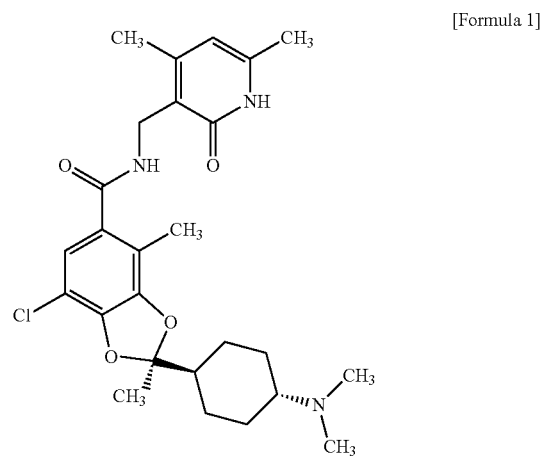 [SMILES: Cc1cc(C)c(CNC(=O)c2cc(Cl)c3c(c2C)O[C@@](C)([C@H]2CC[C@H](N(C)C)CC2)O3)c(=O)[nH]1]

[Formula 1]

(2R)-7-Bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide, or a pharmaceutically acceptable salt thereof:

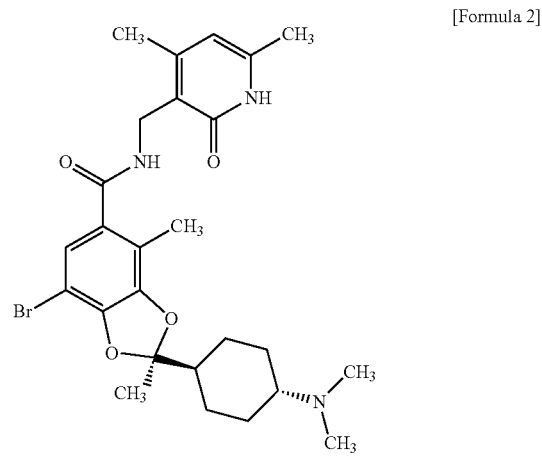 [SMILES: Cc1cc(C)c(CNC(=O)c2cc(Cl)c3c(c2C)O[C@@](C)([C@H]2CC[C@H](N(C)C)CC2)O3)c(=O)[nH]1]

[Formula 2]

The compound of the present invention can optionally be in the form of a pharmaceutically acceptable salt. A pharmaceutically acceptable salt refers to a salt that does not have remarkable toxicity but can be used as a pharmaceutical. The compound of the present invention has a basic group, and hence can be converted into a salt by a reaction with an acid.

Examples of the salt for a basic group include inorganic acid salts such as halogenated hydroacid salts including hydrofluoride, hydrochloride, hydrobromide and hydroiodide, nitrate, perchlorate, sulfate and phosphate; organic acid salts such as $C_1$-$C_6$ alkyl sulfonates including methanesulfonate, trifluoromethanesulfonate, and ethanesulfonate, aryl sulfonates including benzene sulfonate and p-toluenesulfonate, acetate, malate, fumarate, succinate, citrate, ascorbate, tartrate, oxalate, adipate, and maleate; and amino acid salts such as glycine salt, lysine salt, arginine salt, ornithine salt, glutamate and aspartate.

The pharmaceutically acceptable salt of the compound of the present invention may be converted to a hydrate by incorporation of a water molecule in some cases if the salt is left in the air or is reprecipitated, and such a hydrate is embraced in the salt of the present invention.

The pharmaceutically acceptable salt of the compound of the present invention may be converted to a solvate by absorption of some sort of solvent in some cases if the salt is left in the solvent or is reprecipitated, and such a solvate is embraced in the salt of the present invention.

Besides, the present invention also embraces a compound converted, through a reaction with an enzyme, gastric acid or the like under physiological conditions in a living body, into a compound of Example 1 or a compound of Example 2 corresponding to an active ingredient of a pharmaceutical composition of the present invention, namely, a compound converted into the compound of Example 1 or the compound of Example 2 by enzymatic oxidation, reduction, hydrolysis or the like, or a "pharmaceutically acceptable prodrug compound" converted into the compound of Example 1 or the compound of Example 2 by hydrolysis or the like caused by gastric acid or the like.

The compound of the present invention or the pharmaceutically acceptable salt thereof can be isolated and purified by any of known methods, such as extraction, precipitation, distillation, chromatography, separation by precipitation, and reprecipitation.

The compound of the present invention can contain, in one or more atoms constituting the compound, an isotope in a non-natural ratio. Examples of the isotope include heavy hydrogen ($^2$H), tritium ($^3$H), iodine-125 ($^{125}$I) and carbon-14 ($^{14}$C). Besides, the compound can be radiolabeled with a radioactive isotope such as tritium ($^3$H), iodine-125 ($^{125}$I) or carbon-14 ($^{14}$C). The radiolabeled compound is useful as a therapeutic or prophylactic agent, a research reagent such as an assay reagent, and a diagnostic agent such as an in-vivo image diagnostic agent. It is noted that all isotopic variants of the compound of the present invention are embraced in the scope of the present invention no matter whether they are radioactive or not.

The compound of the present invention or the pharmaceutically acceptable salt thereof may be used together with another antitumor agent. Examples of the antitumor agent include an alkylating agent, an antimetabolite, an antitumor antibiotic, an antineoplastic plant extract, a BRM (biological response modifier), a hormone, a vitamin, an antitumor antibody, a molecular targeted drug, and other antitumor agents.

More specifically, examples of the alkylating agent include alkylating agent such as nitrogen mustard, nitrogen mustard N-oxide or chlorambucil, an aziridine-based alkylating agent such as carboquone or thiotepa, an epoxide-based alkylating agent such as di-bromo-mannitol or di-bromo-dulcitol, a nitrosourea-based alkylating agent such as carmustine, lomustine, semustine, nimustine hydrochloride, streptozocin, chlorozotocin, or ranimustine, and busulfan, improsulfan tosilate, and dacarbazine.

Examples of various antimetabolites include a purine antimetabolite such as 6-mercaptopurine, 6-thioguanine or thioinosine, a pyrimidine antimetabolite such as fluorouracil, tegafur, tegafur-uracil, carmofur, doxifluridine, broxuridine, cytarabine, or enocitabine, and a folic acid metabolite such as methotrexate or trimetrexate.

Examples of the antitumor antibiotic include an anthracycline-based antibiotic antitumor agent such as mitomycin C, bleomycin, peplomycin, daunorubicin, aclarbicin, doxorubicin, pirarubicin, THP-adriamycin, 4'-epidoxorubicin, or epirubicin, and chromomycin A3 and actinomycin D.

Examples of the antineoplastic plant extract include vinca alkaloids such as vindesine, vincristine and vinblastine, taxanes such as paclitaxel and docetaxel, and epipodophyllotoxins such as etoposide and teniposide.

Examples of the BRM include a tumor necrosis factor and indomethacin.

Examples of the hormone include hydrocortisone, dexamethasone, methylprednisolone, prednisolone, prasterone, betamethasone, triamcinolone, oxymetholone, nandrolone, methenolone, fosfestrol, ethinylestradiol, chlormadinone and medroxyprogesterone.

Examples of the vitamin include vitamin C and vitamin A.

Examples of the antitumor antibody and the molecular targeted drug include trastuzumab, rituximab, cetuximab, nimotuzumab, denosumab, bevacizumab, infliximab, imatinib mesylate, gefitinib, erlotinib, sunitinib, lapatinib, and sorafenib.

Examples of the other antitumor agents include cisplatin, carboplatin, oxaliplatin, tamoxifen, camptothecin, ifosfamide, cyclophosphamide, melphalan, L-asparaginase, aceglatone, schizophyllan, picibanil, procarbazine, pipobroman, neocarzinostatin, hydroxyurea, ubenimex, and krestin.

The compound of the present invention or the pharmaceutically acceptable salt thereof can be administered in various forms. Examples of the dosage forms include oral administration in the form of a tablet, a capsule, a granule, an emulsion, a pill, a powder, and a syrup (a solution), and parenteral administration in the form of an injection (intravenous, intramuscular, subcutaneous or intraperitoneal administration), a drip infusion, and a suppository (rectal administration). These various preparations can be formulated by an ordinary method using a principal agent together with an auxiliary agent usually used in the field of pharmaceutical formulation, such as an excipient, a binder, a disintegrating agent, a lubricant, a corrigent, a solubilizing agent, a suspension, and a coating agent.

When the compound or the salt is used in the form of a tablet, a carrier to be used can be, for example, an excipient such as lactose, white sugar, sodium chloride, glucose, urea, starch, calcium carbonate, kaolin, crystalline cellulose, or silicic acid; a binder such as water, ethanol, propanol, simple syrup, a glucose solution, a starch solution, a gelatin solution, carboxymethyl cellulose, shellac, methyl cellulose, potassium phosphate, or polyvinyl pyrrolidone; a disintegrating agent such as dry starch, sodium alginate, an agar powder, a laminaran powder, sodium hydrogen carbonate, calcium carbonate, a polyoxyethylene sorbitan fatty acid ester, sodium lauryl sulfate, monoglyceride stearate, starch, or lactose; a disintegration inhibitor such as white sugar, stearin, cacao butter, or a hydrogenated oil; an absorption promoter such as a quaternary ammonium salt, or sodium lauryl sulfate; a moisturizing agent such as glycerin or starch; an adsorbent such as starch, lactose, kaolin, bentonite, or colloidal silicic acid; or a lubricant such as purified talc, stearate salt, a boric acid powder, or polyethylene glycol. Besides, the tablet can be provided with a usual coating if necessary, and can be in the form of, for example, a sugar-coated tablet, a gelatin-coated tablet, an enteric-coated tablet, or a film-coated tablet, or a bilayer tablet or a multilayer tablet.

When the compound or the salt is used in the form of a pill, a carrier to be used can be an excipient such as glucose, lactose, cacao butter, starch, a hydrogenated vegetable oil, kaolin, or talc; a binder such as a gum arabic powder, powdered tragacanth, gelatin, or ethanol; or a disintegrating agent such as laminaran, or agar.

When the compound or the salt is used in the form of a suppository, any of carriers known in this technical field can be widely used, and examples include polyethylene glycol, cacao butter, higher alcohols, esters of higher alcohols, gelatin, and semi-synthetic glycerides.

When used in the form of an injection, the compound or the salt can be used as a solution, an emulsion or a suspension. The solution, the emulsion or the suspension is preferably sterilized, and isotonic to blood. A solvent used for preparing the solution, the emulsion or the suspension is not especially limited as long as the solvent can be used as a diluent for medical use, and examples include water, ethanol, propylene glycol, ethoxylated isostearyl alcohol, polyoxylated isostearyl alcohol, and a polyoxyethylene sorbitan fatty acid ester. In this case, the preparation may contain common salt, glucose or glycerin in an amount sufficient for preparing an isotonic solution, and may contain a usual solubilizing agent, buffer, soothing agent or the like.

Besides, the above-described formulation can contain, if necessary, a colorant, a preservative, a perfume, a flavoring agent, a sweetener or the like, and may further contain another pharmaceutical.

An amount of the compound contained as the active ingredient in the formulation is not especially limited but is appropriately selected from a wide range, and is usually 0.5 to 70% by weight, and preferably 1 to 30% by weight in the entire composition.

The amount of use is varied depending on the symptom, the age and the like of a patient (a warm-blooded animal, particularly a human), and in the case of oral administration, it is preferably administered to an adult once through six times per day depending on the symptom, with the upper limit per day set to 2000 mg (preferably 100 mg) and the lower limit set to 0.1 mg (preferably 1 mg, and more preferably 10 mg).

The present invention provides a method for treating ATL in a patient suffering from ATL, including administering the compound of the present invention or the pharmaceutically acceptable salt thereof to the patient. The present invention also provides a method for preventing onset of ATL in a subject of an HTLV-1 carrier, including administering the compound of the present invention or the pharmaceutically acceptable salt thereof to the subject.

The present invention provides a pharmaceutical composition for use in treating ATL in a patient suffering from ATL, containing the compound of the present invention or the pharmaceutically acceptable salt thereof. The present invention also provides a pharmaceutical composition for use in prevention of onset of ATL in a subject of an HTLV-1 carrier, containing the compound of the present invention or the pharmaceutically acceptable salt thereof.

The pharmaceutical composition of the present invention may contain a pharmaceutically acceptable excipient in addition to the compound of the present invention or the pharmaceutically acceptable salt thereof.

The present invention provides the compound of the present invention or the pharmaceutically acceptable salt thereof for use in treating ATL in a patient suffering from ATL. The present invention also provides the compound of the present invention or the pharmaceutically acceptable salt thereof for use in prevention of onset of ATL in a subject of an HTLV-1 carrier. The present invention provides use of the compound of the present invention or the pharmaceutically acceptable salt thereof in production of a pharmaceutical composition for use in treating ATL in a patient suffering from ATL. The present invention also provides use of the compound of the present invention or the pharmaceutically acceptable salt thereof for use in production of a pharmaceutical composition to be used in prevention of onset of ATL in a subject of an HTLV-1 carrier.

According to Text Examples 1 to 3 described below, the compound of the present invention or the pharmaceutically acceptable salt thereof can reduce growth of adult T cell leukemia/lymphoma, can lower a survival rate of adult T cell leukemia/lymphoma, and/or can kill adult T cell leukemia/lymphoma. Accordingly, the present invention provides a composition or a pharmaceutical composition to be used for reducing growth of adult T cell leukemia/lymphoma, for lowering a survival rate of adult T cell leukemia/lymphoma, and/or for killing adult T cell leukemia/lymphoma, containing the compound of the present invention or the pharmaceutically acceptable salt thereof. The present invention provides use of the compound of the present invention or the pharmaceutically acceptable salt thereof in production of a composition or a pharmaceutical composition to be used for reducing growth of adult T cell leukemia/lymphoma, for lowering a survival rate of adult T cell leukemia/lymphoma, and/or for killing adult T cell leukemia/lymphoma. The present invention provides a method for reducing growth of adult T cell leukemia/lymphoma, for lowering a survival rate of adult T cell leukemia/lymphoma, and/or for killing adult T cell leukemia/lymphoma in a subject requiring this, including administering the compound of the present invention or the pharmaceutically acceptable salt thereof to the subject.

EXAMPLES

Reference Example 1

Methyl 5-chloro-3,4-dihydroxy-2-methylbenzoate

[Formula 3]

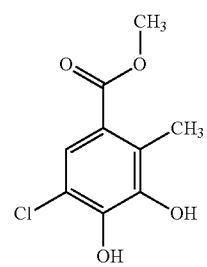

Methyl 3,4-dihydroxy-2-methylbenzoate (12.1 g, 66.2 mmol) was dissolved in ethyl acetate (265 mL), N-chlorosuccinimide (13.3 g, 99.2 mmol) was added thereto, the resultant was stirred at room temperature for 1 hour, and p-anisole (7.15 g, 66.2 mmol) was added to the resultant, followed by stirring another 15 minutes. The thus obtained reaction solution was washed with water and a saturated saline solution, and the resultant was dried over magnesium sulfate and concentrated under reduced pressure. The thus obtained residue was washed with dichloromethane to obtain a title compound (8.03 g, 37.1 mmol, 56% yield).

$^1$H-NMR (400 MHz, DMSO-$d_6$) δ: 2.34 (3H, s), 3.76 (3H, s), 7.36 (1H, s), 9.11 (1H, br s), 9.96 (1H, br s). MS (ESI) m/z: 215 (M−H)$^-$.

Reference Example 2 tert-Butyl N-(trans-4-ethynylcyclohexyl)carbamate

[Formula 4]

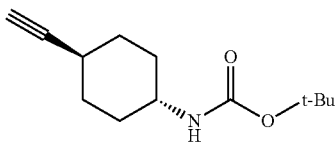

To a methanol solution (30 mL) of tert-butyl N-(trans-4-formylcyclohexyl)carbamate (0.856 g, 3.77 mmol), potassium carbonate (1.04 g, 7.54 mmol) and 1-diazo-1-dimethoxyphophoryl-propan-2-one (0.565 mL, 3.77 mmol) were added, and the resultant was stirred at room temperature for 16 hours. To the thus obtained reaction solution, water was added, the resultant was extracted with ethyl acetate, the resulting organic layer was washed with a saturated saline solution and then dried over anhydrous sodium sulfate. The solvent was distilled off under reduced pressure, and the resulting residue was purified by silica gel chromatography (hexane:ethyl acetate=100:0 to 85:15) to obtain a title compound (0.678 g, 3.04 mmol, 81% yield).

1H-NMR (400 MHz, CDCl3) δ: 1.04-1.17 (2H, m), 1.42-1.55 (2H, m), 1.44 (9H, s), 1.94-2.05 (4H, m), 2.04 (1H, d, J=2.5 Hz), 2.16-2.25 (1H, m), 3.34-3.50 (1H, m), 4.29-4.43 (1H, br s).

Reference Example 3

Methyl 5-bromo-3,4-dihydroxy-2-methylbenzoate

[Formula 5]

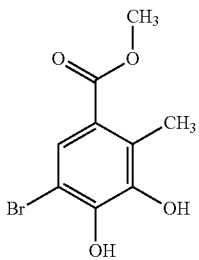

Methyl 3,4-dihydroxy-2-methylbenzoate (43.1 g, 237 mmol) was dissolved in acetic acid (250 mL) and dichloromethane (250 mL), a dichloromethane solution (20 mL) of bromine (37.8 g, 237 mmol) was added thereto in a dropwise manner over 15 minutes while cooling over ice, and the resultant was stirred at the same temperature for 4 hours. Thereafter, bromide (3.78 g, 23.7 mmol) was further added to the resultant, the resulting mixture was stirred for 1.5 hours while cooling over ice, and iced water was added to the resultant reaction solution followed by extraction with ethyl acetate. The resulting organic layer was washed with a sodium sulfite aqueous solution and a saturated saline solution, and was concentrated under reduced pressure. The thus obtained residue was washed with dichloromethane to obtain a title compound (50.4 g, 193 mmol, 82% yield).

$^1$H-NMR (400 MHz, CDCl$_3$) δ: 2.47 (3H, s), 3.87 (3H, s), 5.61 (1H, br s), 5.83 (1H, br s), 7.67 (1H, s). MS (ESI) m/z: 259, 261 (M−H)$^-$.

Example 1

(2R)-7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide

[Formula 6]

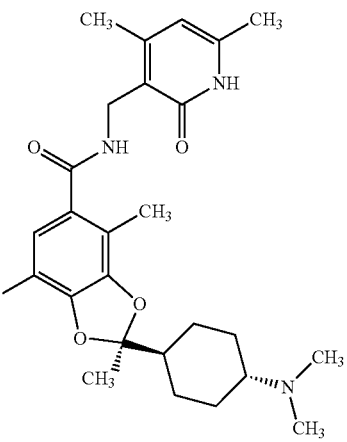

(Step 1-1)

Methyl 2-[trans-4-(tert-butoxycarbonylamino)cyclohexyl]-7-chloro-2,4-dimethyl-1,3-benzodioxole-5-carboxylate To a toluene solution (50 mL) of the methyl 5-chloro-3,4-dihydroxy-2-methylbenzoate (1.00 g, 4.62 mmol) synthesized in Reference Example 1 and the tert-butyl N-(trans-4-ethynylcyclohexyl)carbamate (1.55 g, 6.93 mmol) synthesized in Reference Example 2, triruthenium dodecacarbonyl (0) (0.0738 g, 0.115 mmol) and 5-(di-tert-butylphosphino)-1',3',5'-triphenyl-1'H-[1,4']bipyrazole (0.175 g, 0.346 mmol) were added, and the resultant mixture was stirred under a nitrogen atmosphere at 120° C. for 1 hour. After completing the reaction, the solvent was distilled off under reduced pressure, and the thus obtained residue was purified by silica gel column chromatography (hexane:ethyl acetate=100:0 to 80:20) to obtain a title compound (1.00 g, 2.28 mmol, 49% yield).

$^1$H-NMR (400 MHz, CDCl$_3$) δ: 1.02-1.16 (2H, m), 1.24-1.40 (2H, m), 1.44 (9H, s), 1.62 (3H, s), 1.78-1.88 (1H, m), 1.91-2.00 (2H, m), 2.04-2.12 (2H, m), 2.38 (3H, s), 3.33-3.46 (1H, m), 3.85 (3H, s), 4.37 (1H, br s), 7.53 (1H, s).

(Step 1-2)

Methyl (2R)-2-[trans-4-(tert-butoxycarbonylamino)cyclohexyl]-7-chloro-2,4-dimethyl-1,3-benzodioxole-5-carboxylate From the methyl 2-[trans-4-(tert-butoxycarbonylamino)cyclohexyl]-7-chloro-2,4-dimethyl-1,3-benzodioxole-5-carboxylate synthesized in step 1-1, each enantiomer was separated under the following conditions:

Column: Daicel Corporation, CHIRALCEL OZ-H 4.6 mm ID×250 mm L
Elution Solvent: n-hexane:ethanol=98:2
Flow Rate: 1.00 mL/min
Temperature: 25° C.
First Peak: 10.7 min ($[\alpha]_D^{20}$=−18.3 (C=0.92, chloroform))
Second Peak: 11.7 min ($[\alpha]_D^{20}$=+18.3 (C=0.96, chloroform))

In the following steps, the second peak isolated by using a chiral column for separation was used.

(Step 1-3)

(2R)-2-[trans-4-(tert-Butoxycarbonylamino)cyclohexyl]-7-chloro-2,4-dimethyl-1,3-benzodioxole-5-carboxylic Acid To the methyl (2R)-2-[trans-4-(tert-butoxycarbonylamino)cyclohexyl]-7-chloro-2,4-dimethyl-1,3-benzodioxole-5-carboxylate (the second peak, 0.234 g, 0.532 mmol) separated in step 1-2, tetrahydrofuran (3 mL) and methanol (1.5 mL) were added, and a 1M sodium hydroxide aqueous solution (1.33 mL, 1.33 mmol) was further added to the resultant, followed by stirring at room temperature for 16 hours. After completing the reaction, 1M hydrochloric acid (1.33 mL, 1.33 mmol) was added thereto for neutralization, and dichloromethane was further added thereto for extraction. The thus obtained organic layer was concentrated under reduced pressure to obtain a title compound (0.227 g, 0.532 mmol, 100% yield).

(Step 1-4)

tert-Butyl N-[trans-4-[(2R)-7-chloro-5-[(4,6-dimethyl-2-oxo-1,2-dihydropyridin-3-yl)methylcarbamoyl]-2,4-dimethyl-1,3-benzodioxol-2-yl]cyclohexyl]carbamate To a dimethylformamide solution (5 mL) of the (2R)-2-[trans-4-(tert-butoxycarbonylamino)cyclohexyl]-7-chloro-2,4-dimethyl-1,3-benzodioxole-5-carboxylic acid (0.227 g, 0.532 mmol) synthesized in step 1-3, 3-(aminomethyl)-4,6-dimethyl-1,2-dihydropyridin-2-one hydrochloride (0.116 g, 0.586 mmol), 1-ethyl-3-(3-dimethylaminopropyl)carbodiimide hydrochloride (0.122 g, 0.639 mmol), 1-hydroxy-7-azabenzotriazole (0.0869 g, 0.639 mmol), and N,N-diisopropylethylamine (0.223 mL, 1.28 mmol) were added, and the resultant was stirred under a nitrogen atmosphere at room temperature for 1.5 hours. After completing the reaction, a saturated sodium hydrogen carbonate aqueous solution was added to the reaction solution, and the resultant was extracted with ethyl acetate. The resulting organic layer was dried over anhydrous sodium sulfate, and the solvent was distilled off under reduced pressure. The thus obtained residue was dissolved in chloroform, and purified by the silica gel column chromatography (chloroform:methanol=100:0 to 95:5) to obtain a title compound (0.298 g, 0.532 mmol, 100% yield).

$^1$H-NMR (400 MHz, CDCl$_3$) δ: 1.01-1.16 (2H, m), 1.23-1.38 (2H, m), 1.44 (9H, s), 1.59 (3H, s), 1.76-1.84 (1H, m), 1.88-1.95 (2H, m), 2.02-2.11 (2H, m), 2.22 (3H, s), 2.25 (3H, s), 2.37 (3H, s), 3.30-3.46 (1H, m), 4.35-4.41 (1H, m), 4.49 (2H, d, J=6.1 Hz), 5.96 (1H, s), 6.87 (1H, s), 7.23 (1H, t, J=6.1 Hz). MS (APCI) m/z: 560 (M+H)$^+$.

(Step 1-5)

(2R)-2-(trans-4-Aminocyclohexyl)-7-chloro-N-[(4,6-dimethyl-2-oxo-1,2-dihydropyridin-3-yl)methyl]-2,4-dimethyl-1,3-benzodioxole-5-carboxamide The tert-butyl N-[trans-4-[(2R)-7-chloro-5-[(4,6-dimethyl-2-oxo-1,2-dihydropyridin-3-yl)methylcarbamoyl]-2,4-dimethyl-1,3-benzodioxol-2-yl]cyclohexyl]carbamate (0.298 g, 0.532 mmol) synthesized in step 1-4 was dissolved in methanol (1.3 mL), and a 4M hydrochloric acid-1,4-dioxane solution (1.33 mL, 5.32 mmol) was added thereto followed by stirring at room temperature for 1 hour. After completing the reaction, a saturated sodium bicarbonate aqueous solution was added thereto for neutralization, and 20% methanol-chloroform was used for extraction. The resulting organic layer was washed with a saturated saline solution, dried over sodium sulfate, and then concentrated under reduced pressure to obtain a title compound (0.241 g, 0.524 mmol, 98% yield).

MS (APCI) m/z: 460 (M+H)$^+$.

(Step 1-6)

(2R)-7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide The (2R)-2-(trans-4-aminocyclohexyl)-7-chloro-N-[(4,6-dimethyl-2-oxo-1,2-dihydropyridin-3-yl)methyl]-2,4-dimethyl-1,3-benzodioxole-5-carboxamide (17.0 g, 36.9 mmol) synthesized in step 1-5 was dissolved in methanol (200 mL), a 37% formaldehyde aqueous solution (6.29 g, 77.5 mmol) was added thereto, the resultant was stirred at room temperature for 10 minutes, and sodium triacetoxyborohydride (34.2 g, 129 mmol) was added thereto, followed by stirring at room temperature for 16 hours. After completing the reaction, the resultant was neutralized with a 1M sodium hydroxide aqueous solution, and 20% methanol-chloroform was used for extraction. The resulting organic layer was washed with a saturated saline solution, dried over sodium sulfate, and concentrated under reduced pressure, and the thus obtained residue was purified by basic silica gel column chromatography (ethyl acetate:methanol=100:0 to 96:4) to obtain a title compound (15.3 g, 31.4 mmol, 85% yield).

$^1$H-NMR (400 MHz, DMSO-d$_6$) δ: 1.08-1.21 (4H, m), 1.59 (3H, s), 1.77-1.90 (5H, m), 2.03-2.09 (1H, m), 2.11 (6H, s), 2.13 (6H, s), 2.16 (3H, s), 4.21 (2H, d, J=4.9 Hz), 5.85 (1H, s), 6.84 (1H, s), 8.13 (1H, t, J=4.9 Hz), 11.48 (1H, s).

MS (APCI) m/z: 488 (M+H)$^+$.

Specific rotation $[\alpha]_D^{20}$=+1.0 (C=1.0, chloroform)

Example 2

(2R)-7-Bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide

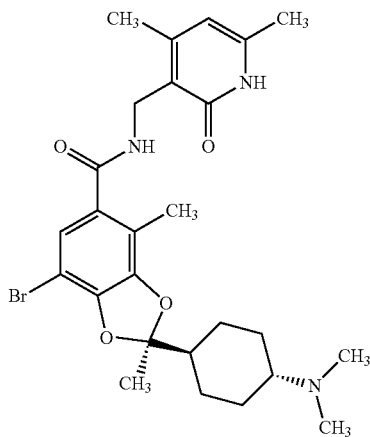

[Formula 7]

(Step 2-1)

Methyl 7-bromo-2-[trans-4-(tert-butoxycarbonylamino)cyclohexyl]-2,4-dimethyl-1,3-benzodioxole-5-carboxylate A reaction similar to that of step 1-1 was performed by using the methyl 5-bromo-3,4-dihydroxy-2-methylbenzoate (23.5 g, 90.0 mmol) synthesized in Reference Example 3, the tert-butyl N-(trans-4-ethynylcyclohexyl)carbamate (22.1 g, 99.0 mmol) synthesized in Reference Example 2, triruthenium dodecacarbonyl (0) (1.44 g, 2.25 mmol) and 5-(di-tert-butylphosphino)-1',3',5'-triphenyl-1'H-[1,4']bipyrazole (3.42 g, 6.75 mmol) to obtain a title compound (38.9 g, 80.3 mmol, 89% yield).

$^1$H-NMR (400 MHz, CDCl$_3$) δ: 1.04-1.15 (2H, m), 1.25-1.38 (2H, m), 1.44 (9H, s), 1.63 (3H, s), 1.79-1.87 (1H, m), 1.91-1.99 (2H, m), 2.04-2.12 (2H, m), 2.38 (3H, s), 3.31-3.46 (1H, m), 3.84 (3H, s), 4.37 (1H, br s), 7.67 (1H, s).

(Step 2-2)

(2R)-Methyl 7-bromo-2-[trans-4-(tert-butoxycarbonylamino)cyclohexyl]-2,4-dimethyl-1,3-benzodioxole-5-carboxylate From the methyl 7-bromo-2-[trans-4-(tert-butoxycarbonylamino)cyclohexyl]-2,4-dimethyl-1,3-benzodioxole-5-carboxylate synthesized in step 2-1, each enantiomer was separated under the following conditions:

Column: Daicel Corporation, CHIRALCEL OZ-H 4.6 mm ID×250 mm L
Elution Solvent: n-hexane:ethanol=98:2
Flow Rate: 1.00 mL/min
Temperature: 25° C.
First Peak: 11.2 min (specific rotation $[\alpha]_D^{20}$=−6.5 (C=1.0, chloroform))
Second Peak: 12.3 min (specific rotation $[\alpha]_D^{20}$=+6.3 (C=1.0, chloroform))

In the following steps, the second peak isolated by using a chiral column for separation was used.

(Step 2-3)

(2R)-7-Bromo-2-[trans-4-(tert-butoxycarbonylamino)cyclohexyl]-2,4-dimethyl-1,3-benzodioxole-5-carboxylic Acid A reaction similar to that of step 1-3 was performed by using the (2R)-methyl 7-bromo-2-[trans-4-(tert-butoxycarbonylamino)cyclohexyl]-2,4-dimethyl-1,3-benzodioxole-5-carboxylate (the second peak, 0.956 g, 1.97 mmol) separated in step 2-2, tetrahydrofuran (6 mL), methanol (3 mL), and a 1M sodium hydroxide aqueous solution (2.96 mL, 2.96 mmol) to obtain a title compound (0.903 g, 1.92 mmol, 97% yield).

(Step 2-4)

tert-Butyl N-[trans-4-[(2R)-7-bromo-5-[(4,6-dimethyl-2-oxo-1,2-dihydropyridin-3-yl)methylcarbamoyl]-2,4-dimethyl-1,3-benzodioxol-2-yl]cyclohexyl] carbamate A reaction similar to that of step 1-4 was performed by using the (2R)-7-bromo-[trans-4-(tert-butoxycarbonylamino)cyclohexyl]-2,4-dimethyl-1,3-benzodioxole-5-carboxylic acid (0.903 g, 1.92 mmol) synthesized in step 2-3, dimethylformamide (20 mL), 3-(aminomethyl)-4,6-dimethyl-1,2-dihydropyridin-2-one hydrochloride (0.399 g, 2.11 mmol), 1-ethyl-3-(3-dimethylaminopropyl)carbodiimide hydrochloride (0.442 g, 2.30 mmol), 1-hydroxy-7-azabenzotriazole (0.314 g, 2.30 mmol), and N,N-diisopropylethylamine (0.803 mL, 4.61 mmol) to obtain a title compound (0.801 g, 1.32 mmol, 69% yield).

$^1$H-NMR (400 MHz, CDCl$_3$) δ: 1.03-1.15 (2H, m), 1.21-1.38 (2H, m), 1.44 (9H, s), 1.59 (3H, s), 1.75-1.84 (1H, m), 1.89-1.97 (2H, m), 2.02-2.10 (2H, m), 2.21 (3H, s), 2.26 (3H, s), 2.37 (3H, s), 3.34-3.45 (1H, m), 4.41-4.45 (1H, m), 4.49 (2H, d, J=6.0 Hz), 5.95 (1H, s), 7.00 (1H, s), 7.18 (1H, t, J=6.0 Hz). MS (APCI) m/z: 604, 606 (M+H)$^+$.

(Step 2-5)

(2R)-2-(trans-4-Aminocyclohexyl)-7-bromo-N-[(4,6-dimethyl-2-oxo-1,2-dihydropyridin-3-yl)methyl]-2,4-dimethyl-1,3-benzodioxole-5-carboxamide A reaction similar to that of step 1-5 was performed by using the tert-butyl N-[trans-4-[(2R)-7-boromo-5-[(4,6-dimethyl-2-oxo-1,2-dihydropyridin-3-yl)methylcarbamoyl]-2,4-dimethyl-1,3-benzodioxol-2-yl]cyclohexyl]carbamate (0.801, g, 1.32 mmol) synthesized in step 2-4, methanol (1.5 mL), and a 4M hydrochloric acid-1,4-dioxane solution (1.67 mL, 6.62 mmol) to obtain a title compound (0.668 g, 1.32 mmol, 100% yield).

$^1$H-NMR (400 MHz, DMSO-d$_6$) δ: 0.93-1.05 (2H, m), 1.08-1.23 (2H, m), 1.59 (3H, s), 1.73-1.85 (5H, m), 2.10 (3H, s), 2.11 (3H, s), 2.16 (3H, s), 2.39-2.49 (1H, m), 4.21 (2H, d, J=4.9 Hz), 5.85 (1H, s), 6.94 (1H, s), 8.14 (1H, t, J=4.9 Hz).

MS (ESI) m/z: 504, 506 (M+H)$^+$.

(Step 2-6)

(2R)-7-Bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide A reaction similar to that of step 1-6 was performed by using the (2R)-2-(trans-4-aminocyclohexyl)-7-bromo-N-

[(4,6-dimethyl-2-oxo-1,2-dihydropyridin-3-yl)methyl]-2,4-dimethyl-1,3-benzodioxole-5-carboxamide (21.1 g, 41.7 mmol) synthesized in step 2-5, methanol (250 mL), a 37% formaldehyde aqueous solution (7.12 g, 87.8 mmol), and sodium triacetoxyborohydride (38.8 g, 146 mmol) to obtain a title compound (15.1 g, 28.4 mmol, 68% yield).

$^1$H-NMR (400 MHz, DMSO-$d_6$) δ: 1.08-1.20 (4H, m), 1.59 (3H, s), 1.75-1.90 (5H, m), 2.02-2.12 (1H, m), 2.09 (3H, s), 2.11 (3H, s), 2.13 (6H, s), 2.16 (3H, s), 4.21 (2H, d, J=4.9 Hz), 5.85 (1H, s), 6.93 (1H, s), 8.12 (1H, t, J=4.9 Hz), 11.47 (1H, s).

MS (APCI) m/z: 532, 534 (M+H)$^+$.

Specific rotation $[α]_D^{20}$=−7.2 (C=1.0, chloroform)

Example 3

7-Bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide

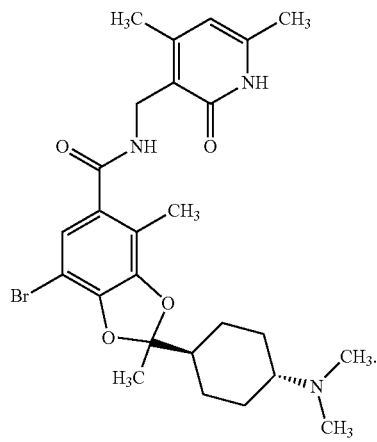

[Formula 8]

(Step 3-1)

7-Bromo-2-[trans-4-(tert-butoxycarbonylamino)cyclohexyl]-2,4-dimethyl-1,3-benzodixole-5-carboxylic Acid A reaction similar to that of step 1-3 was performed by using the methyl 7-bromo-2-[trans-4-(tert-botoxycarbonylamino)cyclohexyl]-2,4-dimethyl-1,3-benzodioxole-5-carboxylate (23.5 g, 48.5 mmol) synthesized in step 2-1, tetrahydrofuran (120 mL), methanol (60 mL), and a 1M sodium hydroxide aqueous solution (72.8 mL, 72.8 mmol) to obtain a title compound (22.8 g, 48.5 mmol, 100% yield).

$^1$H-NMR (CDCl$_3$) δ: 1.04-1.16 (2H, m), 1.25-1.38 (2H, m), 1.44 (9H, s), 1.64 (3H, s), 1.80-1.90 (1H, m), 1.92-2.00 (2H, m), 2.06-2.16 (2H, m), 2.41 (3H, s), 3.35-3.48 (1H, m), 4.40 (1H, br s), 7.80 (1H, s).

MS (ESI) m/z: 468, 470 (M−H)$^−$.

(Step 3-2)

tert-Butyl N-[trans-4-[(7-bromo-5-[(4,6-dimethyl-2-oxo-1H-pyridin-3-yl)methylcarbamoyl]-2,4-dimethyl-1,3-benzodioxol-2-yl]cyclohexyl]carbamate A reaction similar to that of step 1-4 was performed by using the 7-bromo-2-[trans-4-(tert-butoxycarbonylamino)cyclohexyl]-2,4-dimethyl-1,3-benzodioxole-5-carboxylic acid (22.8 g, 48.5 mmol) synthesized in step 3-2, dimethylformamide (300 mL), 3-(aminomethyl)-4,6-dimethyl-1,2-dihydropyridin-2-one hydrochloride (10.1 g, 53.4 mmol), 1-ethyl-3-(3-dimethylaminopropyl)carbodiimide hydrochloride (11.2 g, 58.2 mmol), 1-hydroxy-7-azabenzotriazole (7.92 g, 58.2 mmol), and N,N-diisopropylethylamine (20.3 mL, 146 mmol) to obtain a title compound (26.8 g, 44.3 mmol, 91% yield).

$^1$H-NMR (400 MHz, CDCl$_3$) δ: 1.02-1.15 (2H, m), 1.23-1.40 (2H, m), 1.43 (9H, s), 1.59 (3H, s), 1.75-1.84 (1H, m), 1.89-1.97 (2H, m), 2.02-2.10 (2H, m), 2.21 (3H, s), 2.26 (3H, s), 2.37 (3H, s), 3.34-3.45 (1H, m), 4.39 (1H, d, J=8.4 Hz), 4.49 (2H, d, J=5.5 Hz), 5.96 (1H, s), 7.00 (1H, s), 7.21 (1H, t, J=5.5 Hz).

MS (ESI) m/z: 604, 606 (M+H)$^+$.

(Step 3-3)

(2R)-2-(trans-4-Aminocyclohexyl)-7-bromo-N-[(4,6-dimethyl-2-oxo-1,2-dihydropyridin-3-yl)methyl]-2,4-dimethyl-1,3-benzodioxole-5-carboxamide A reaction similar to that of step 1-5 was performed by using the tert-butyl N-[trans-4-[7-bromo-5-[(4,6-dimethyl-2-oxo-1,2-dihydropyridin-3-yl)methylcarbamoyl]-2,4-dimethyl-1,3-benzodioxol-2-yl]cyclohexyl]carbamate (6.04 g, 9.99 mmol) synthesized in step 3-2, methanol (10 mL), and a 4M hydrochloric acid-1,4-dioxane solution (12.5 mL, 50.0 mmol) to obtain a title compound (4.20 g, 8.30 mmol, 83% yield).

$^1$H-NMR (400 MHz, DMSO-$d_6$) δ: 0.93-1.05 (2H, m), 1.08-1.23 (2H, m), 1.59 (3H, s), 1.73-1.85 (5H, m), 2.10 (3H, s), 2.11 (3H, s), 2.16 (3H, s), 2.39-2.49 (1H, m), 4.21 (2H, d, J=4.9 Hz), 5.85 (1H, s), 6.94 (1H, s), 8.14 (1H, t, J=4.9 Hz).

MS (ESI) m/z: 504, 506 (M+H)$^+$.

(Step 3-4)

7-Bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide A reaction similar to that of step 1-6 was performed by using the 2-(trans-4-aminocyclohexyl)-7-bromo-N-[(4,6-dimethyl-2-oxo-1,2-dihydropyridin-3-yl)methyl]-2,4-dimethyl-1,3-benzodioxole-5-carboxamide (21.0 g, 41.6 mmol) synthesized in step 3-3, dichloromethane (500 mL), a 37% formaldehyde aqueous solution (8.45 g, 104 mmol), and sodium triacetoxyborohydride (55.2 g, 208 mmol) to obtain a title compound (20.0 g, 37.6 mmol, 90% yield). $^1$H-NMR (400 MHz, DMSO-$d_6$) δ: 1.08-1.23 (4H, m), 1.59 (3H, s), 1.75-1.90 (5H, m), 2.02-2.09 (1H, m), 2.10 (3H, s), 2.11 (3H, s), 2.13 (6H, s), 2.16 (3H, s), 4.21 (2H, d, J=4.9 Hz), 5.85 (1H, s), 6.94 (1H, s), 8.14 (1H, t, J=4.9 Hz), 11.48 (1H, s).

MS (APCI) m/z: 532, 534 (M+H)$^+$.

Example 4

(2R)-7-Chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide p-toluenesulfonate To the (2R)-7-chloro-2-[trans-4-(dimethylamino)cyclohexyl]-N-[(4,6-dimethyl-2-oxo-1,2-dihydropyridin-3-yl)

methyl]-2,4-dimethyl-1,3-benzodioxole-5-carboxamide (0.202 g, 0.414 mmol) synthesized in Example 1, acetone (7.97 mL) and a 4.00 mol/L p-toluenesulfonic acid aqueous solution (0.103 mL, 0.414 mmol) were added at room temperature. Thereafter, the resulting solution was stirred at 40° C. for about 20 hours, followed by stirring at room temperature for about 0.5 hours, and then the precipitated solid was filtered off. Subsequently, the solid was dried overnight at room temperature to obtain a title compound (0.256 g, 99% yield).

$^1$H-NMR (DMSO-$d_6$) δ: 1.15-1.32 (2H, m), 1.36-1.50 (2H, m), 1.62 (3H, s), 1.88-2.06 (5H, m), 2.11 (3H, s), 2.12 (3H, s), 2.17 (3H, s), 2.29 (3H, s), 2.70 (3H, s), 2.71 (3H, s), 3.10-3.22 (1H, m), 4.22 (2H, d, J=5.0 Hz), 5.86 (1H, s), 6.87 (1H, s), 7.11 (2H, d, J=8.2 Hz), 7.48 (2H, d, J=8.2 Hz), 8.14 (1H, t, J=5.0 Hz), 9.31 (1H, br s), 11.48 (1H, s).

Elemental analysis Anal. Calcd for $C_{26}H_{34}ClN_3O_4 \cdot C_7H_8O_3S$: C, 60.03; H, 6.41; N, 6.36; Cl, 5.37; S, 4.86. Found: C, 58.81; H, 6.48; N, 6.21; Cl, 5.32; S, 4.85.

Test Example 1

Growth Inhibition Effect Against TL-Om1

Figure 1B:
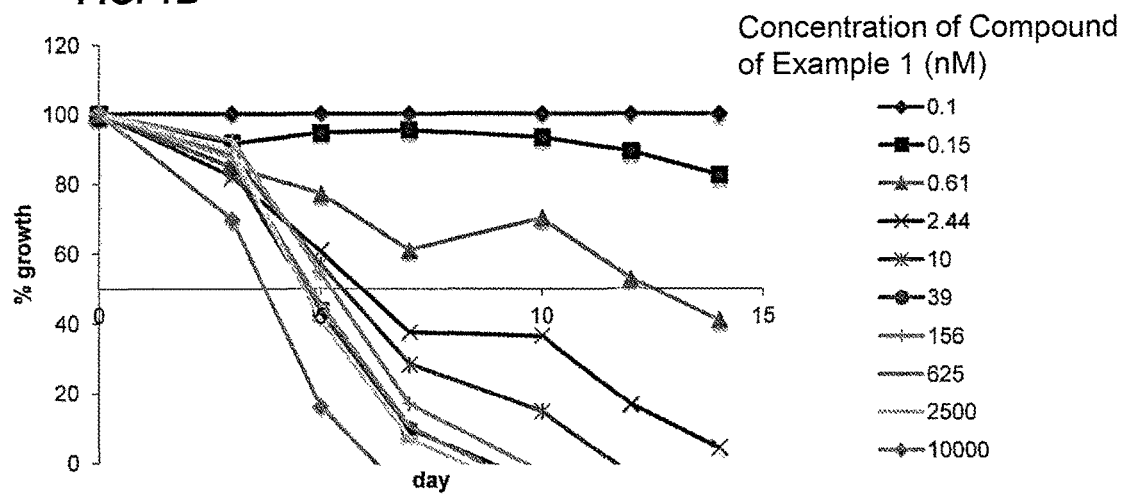
Figure 2A:
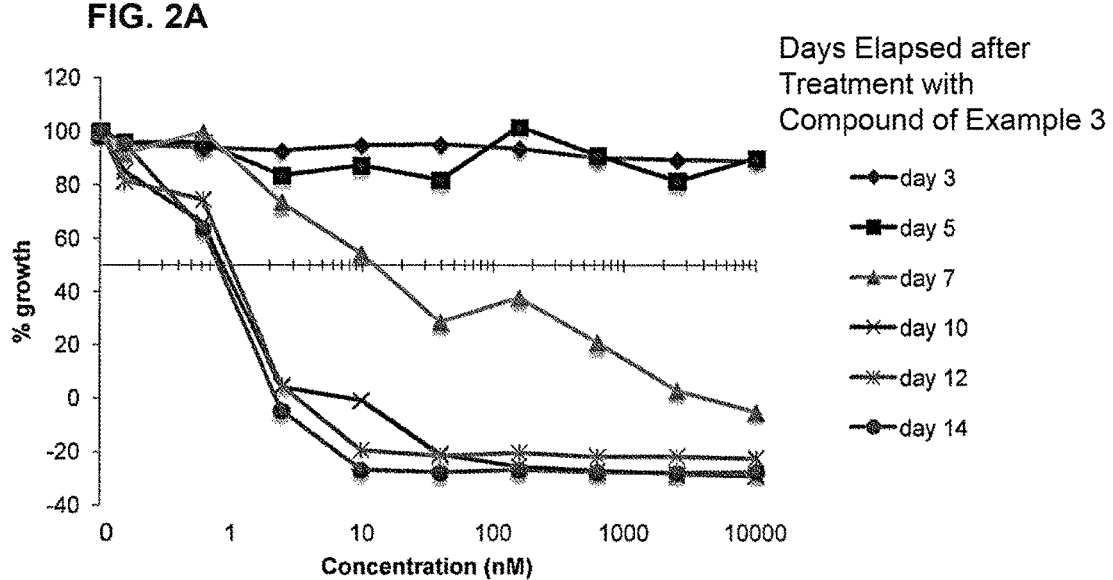
Figure 2B:
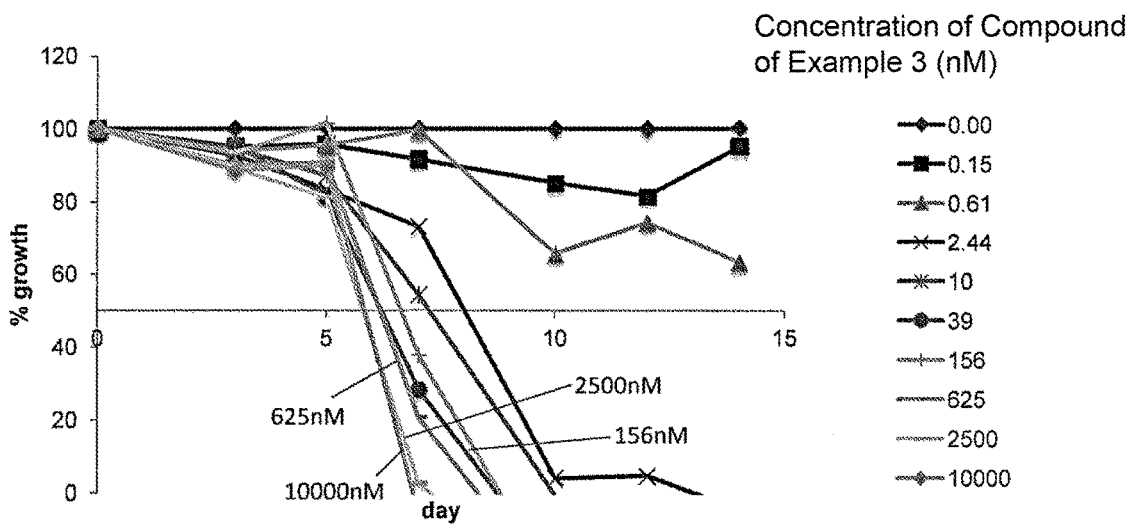

A cell line TL-Om1 derived from an ATL patient tumor cell was provided by Dr. Kazuo Sugamura, Chief Executive, Local Incorporated Administrative Agency Miyagi Prefectural Hospital Organization. The cell line TL-Om1 was suspended in a medium (RPMI 1640 medium (Invitrogen) supplemented with 10% fetal bovine serum (FBS, Invitrogen)), and seeded in a 12-well plate at a density of $1\times10^5$ cells/1 mL/well. Immediately after the seeding, a dilution series of the compound of Example 1 or Example 3 prepared by using DMSO was added thereto, and the resultant was cultured under conditions of 37° C. and 5% $CO_2$. The cells were collected every two or three days, and passage-cultured by transferring 300 μL of the culture medium to a 12-well plate containing 1 mL of a fresh medium. Besides, the dilution series of the compound of Example 1 or Example 3 was added again to continuously carry out the cultivation. On days 3, 5, 7, 10, 12 and 14 after starting the cultivation, the cells were collected from the culture medium to obtain a cell density, and thus, the influence of the compound of Example 1 or Example 3 on the cell growth was examined. The number of cells on each of these days was obtained by WST-8 (Dojindo Laboratories). The cultured cells were seeded in a 96-well plate by 100 μL, WST-8 was added to each well to a final concentration of 10%, and the resultant plate was incubated at 37° C. for 2 hours. An absorbance at 450 nm of each sample was measured by using a plate reader (iMark Microplate Reader, Biorad). A calibration curve between the number of cells and the absorbance was obtained, and the number of cells was calculated on the basis of the absorbance obtained in an actual test. The number of cells was calculated in each passage, and the cell growth rate of each compound-treated group was calculated assuming that the cell growth of a DMSO-treated group was 100%. The results are illustrated in FIGS. 1 and 2.

Test Example 2

Growth Inhibition Effect in ATL Patient-derived Sample

Figure 3:
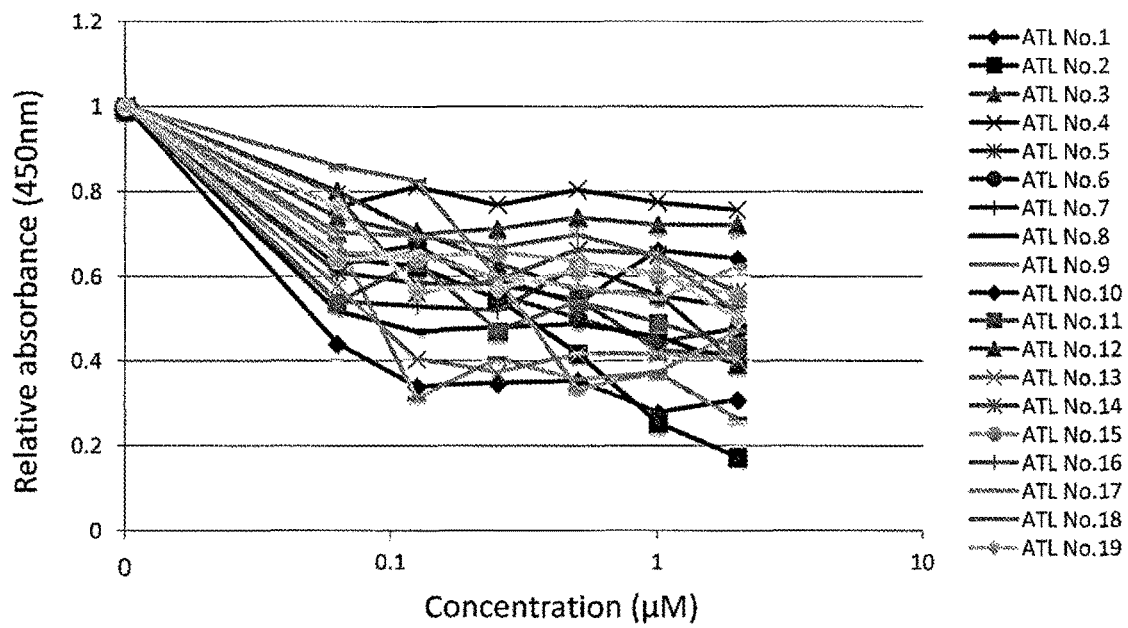
FIG. 3 illustrates an effect of the compound of the present invention on growth of peripheral blood mononuclear cells isolated from ATL patients (26 cases).
Figure 3:
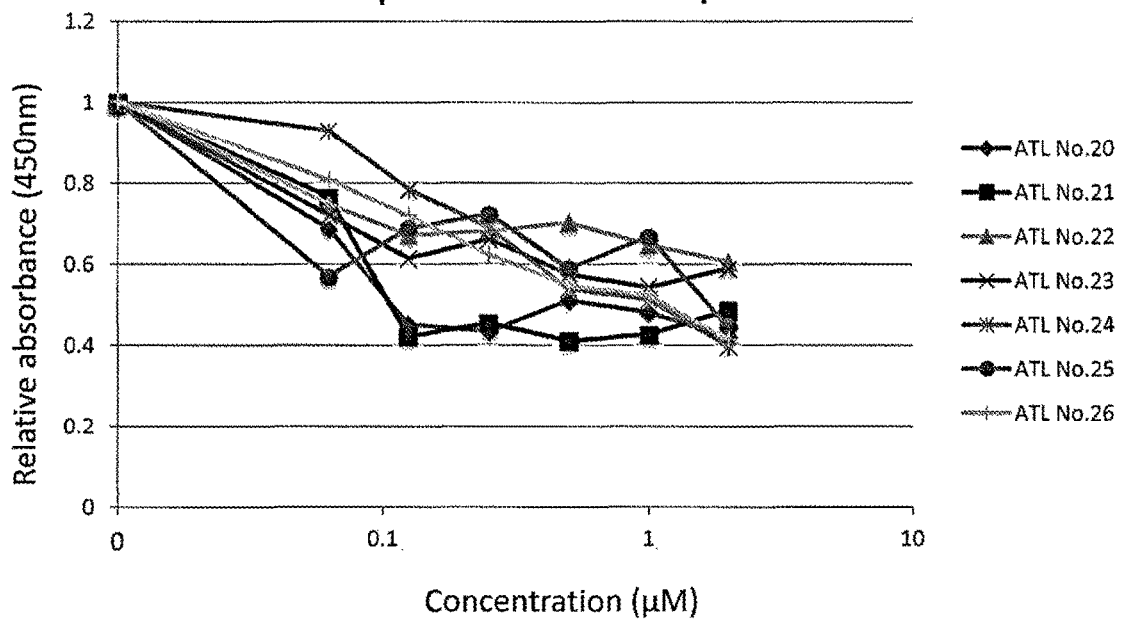

As ATL patient-derived peripheral blood, samples diagnosed as ATL in accordance with criteria of WHO classification and Shimoyama classification (Yamaguchi K., Watanabe T. (2002)) in facilities registered in Joint Study on Predisposing Factors of ATL Development (JSPFAD) were used. From the whole blood of ATL patients of 26 cases (including 19 cases for the compound of Example 1; and 7 cases for the compound of Example 3), peripheral blood monocular cells (PBMCs) containing tumor cells were obtained by centrifugation using Ficoll (GE Healthcare). The PBMCs were suspended in a medium (PRMI 1640 medium supplemented with 10% patient plasma), and seeded in a 48-well plate at a density of $3\times10^5$ cells/300 μL/well (ATL Nos. 1 to 5) or $2\times10^5$ cells/300 μL/well (ATL Nos. 6 to 26). Besides, in order to retain long-term cultivation of ATL cells expressing IL-2R ((CD25), IL-2 (R & C Systems, Inc.) was added thereto to a final concentration of 10 ng/mL. After seeding the cells, a dilution series of each compound prepared by using DMSO was added thereto, and the resultant was cultured under conditions of 37° C. and 5% $CO_2$ for 7 days. The thus cultured cells were seeded in a 96-well plate by 100 μL, WST-8 was added to each well to a final concentration of 10%, the resulting plate was incubated at 37° C. for 4 hours, and an absorbance at 450 nm was measured as an index of the cell density in the medium solution. The results are illustrated in FIG. 3. As a result, it was revealed that the compound of the present invention can be used for treating ATL.

Test Example 3

PVL Reduction Effect in Carrier-Derived Sample

From whole blood of 9 cases diagnosed as an HTLV-1 carrier by an antibody test in facilities registered in JSPFAD, PBMCs containing HTLV-1 infected cells were obtained by centrifugation using Ficoll. The PBMCs were suspended in a medium (RPMI 1640 medium supplemented with 10% FBS), and seeded in a 48-well plate at a density of $5\times10^5$ cells/250 μL/well. Thereafter, DMSO or the compound of Example 1 or Example 3 in a final concentration of 100 nM was added thereto, and the resultant was cultured under conditions of 37° C. and 5% $CO_2$ for 10 to 12 days. The cultured cells were collected, and genomic DNA was extracted therefrom by using QIAmp DNA Blood Mini Kit (QIAGEN). As a ratio of infected cells in a cell population thus cultured, copy number of HTLV-1 was measured by using a real time PCR system (7500 Real Time PCR System, Applied Biosystems, Inc.). As an internal control, the number of RNase P genes was simultaneously measured to calculate the ratio of infected cells (PVL). Primers and a probe used in the real time PCR had the following sequences:

Forward Primer pX2-S

5'-CGGATACCCAGTCTACGTGTT-3'

Reverse Primer pX2-AS

5'-CAGTAGGGCGTGACGATGTA-3'

FAM-Labeled pX2 Probe

5'-CTGTGTACAAGGCGACTGGTGCC-3' [Formula 9]

A primer and a probe for the RNase P genes were purchased from Applied Biosystems, Inc.

Figure 4:
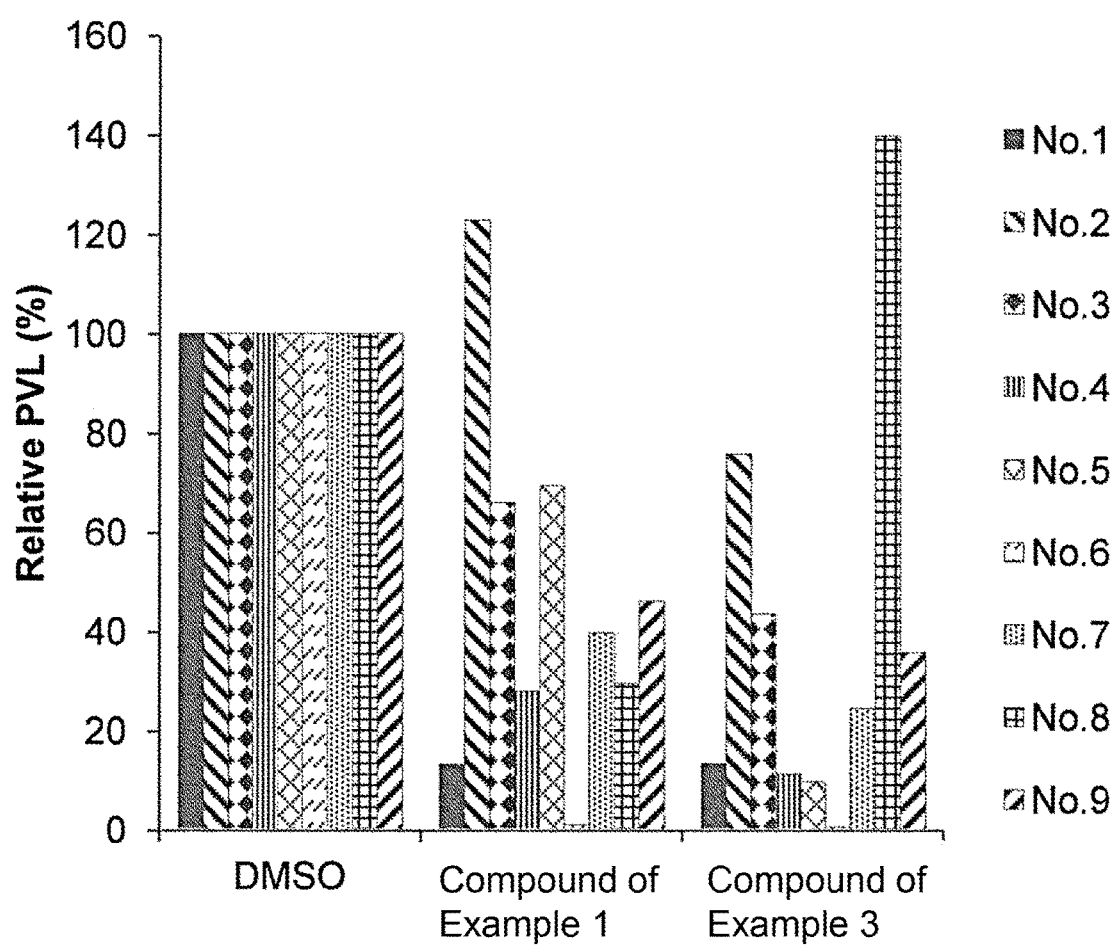
FIG. 4 illustrates an effect of the compound of the present invention on a ratio of infected cells (PVL) in peripheral blood mononuclear cells isolated from HTLV-1 carrier samples.

Assuming that the PVL of the DMSO-treated group was 100%, relative PVL change was calculated and illustrated in FIG. 4. In groups treated with the present compound, PVL was remarkably lowered as compared with that of the DMSO-treated group. As a result, it was revealed that the compound of the present invention lowers the incidence rate of ATL in an HTLV-1 carrier.

It was revealed, as a result of Test Example 1, that an EZH1/2 inhibiting compound dose-dependently and significantly reduced the cell growth of TL-Om1 cells. Besides, the compound significantly reduced cell survival of ATL patient-derived tumor cells. Furthermore, it was confirmed that the ratio of HTLV-1 infected cells present in the carrier peripheral blood was remarkably reduced. This suggests that the compound induces cell death of the HTLV-1 infected cells.

The invention claimed is:

1. A method for treating adult T cell leukemia/lymphoma in a patient suffering from adult T cell leukemia/lymphoma, comprising administering, to the patient, 7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, or 7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

2. A method for treating adult T cell leukemia/lymphoma in a patient suffering from adult T cell leukemia/lymphoma, comprising administering, to the patient, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

3. A method for treating adult T cell leukemia/lymphoma in a patient suffering from adult T cell leukemia/lymphoma, comprising administering, to the patient, (2R)-7-bromo-2-[trans-4-(dimethylamino)cyclohexyl]-N-[(4, 6-dimethyl-2-oxo-1,2-dihydropyridin-3-yl)methyl]-2,4-dimethyl-1,3-benzodioxole-5-carboxamide or a pharmaceutically acceptable salt thereof.

4. A method for reducing onset of adult T cell leukemia/lymphoma in a human subject who is a carrier of human adult T cell leukemia virus type I (HTLV-1), comprising administering, to the subject, 7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof, or 7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

5. A method for reducing onset of adult T cell leukemia/lymphoma in a human subject who is a carrier of human adult T cell leukemia virus type I (HTLV-1), comprising administering, to the subject, (2R)-7-chloro-2-[trans-4-(dimethylamino)cyclohexyl]-N-[(4, 6-dimethyl-2-oxo-1,2-dihydropyridin-3-yl)methyl]-2,4-dimethyl-1,3-benzodioxole-5-carboxamide or a pharmaceutically acceptable salt thereof.

6. A method for reducing onset of adult T cell leukemia/lymphoma in a human subject who is a carrier of human adult T cell leukemia virus type I (HTLV-1), comprising administering, to the subject, (2R)-7-bromo-2-[trans-4-(dimethylamino)cyclohexyl]-N-[(4, 6-dimethyl-2-oxo-1,2-dihydropyridin-3-yl)methyl]-2,4-dimethyl-1,3-benzodioxole-5-carboxamide or a pharmaceutically acceptable salt thereof.

7. A method for treating a human adult T cell leukemia virus type I (HTLV-1) carrier, comprising administering, to the subject, (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

8. A method for treating a human adult T cell leukemia virus type I (HTLV-1) carrier, comprising administering, to the subject, (2R)-7-bromo-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide or a pharmaceutically acceptable salt thereof.

* * * * *